United States Patent [19]  [11] 4,409,850
Zeck  [45] Oct. 18, 1983

[54] PORTABLE SAMPLE VESSEL

[76] Inventor: Ted E. Zeck, P.O. Box 176, Snyder, Tex. 79549

[21] Appl. No.: 354,734

[22] Filed: Mar. 4, 1982

[51] Int. Cl.³ .............................................. G01N 1/14
[52] U.S. Cl. .............................. 73/864.62; 73/864.91; 366/130
[58] Field of Search ........................ 73/864.62, 864.91; 366/130, 349

[56]   References Cited
U.S. PATENT DOCUMENTS 2,636,387  4/1953  McKinney et al. ............. 73/864.62
3,789,670  2/1974  Rosenwald ...................... 73/864.62
3,793,888  2/1974  Rosenwald ...................... 73/864.62

Primary Examiner—Anthony V. Ciarlante
Assistant Examiner—John Chapman
Attorney, Agent, or Firm—Wendell Coffee

[57]  ABSTRACT

A large diameter ball is placed within the sample cavity of a liquified petroleum gas sample vessel or cell. After the sample has been taken, the entire cell may be shaken to cause the ball to break up stratification, and to mix the sample. When a vessel or cell is emptied, a ball fits within hemispherical cavities between a piston and an end. The large diameters of the ball and cavities result in shoulders or ledges, which are less than half the diameter of the ball, so that they do not prohibit the movement of the piston because the ball will be forced into the cavities regardless of the orientation of the cell.

1 Claim, 1 Drawing Figure

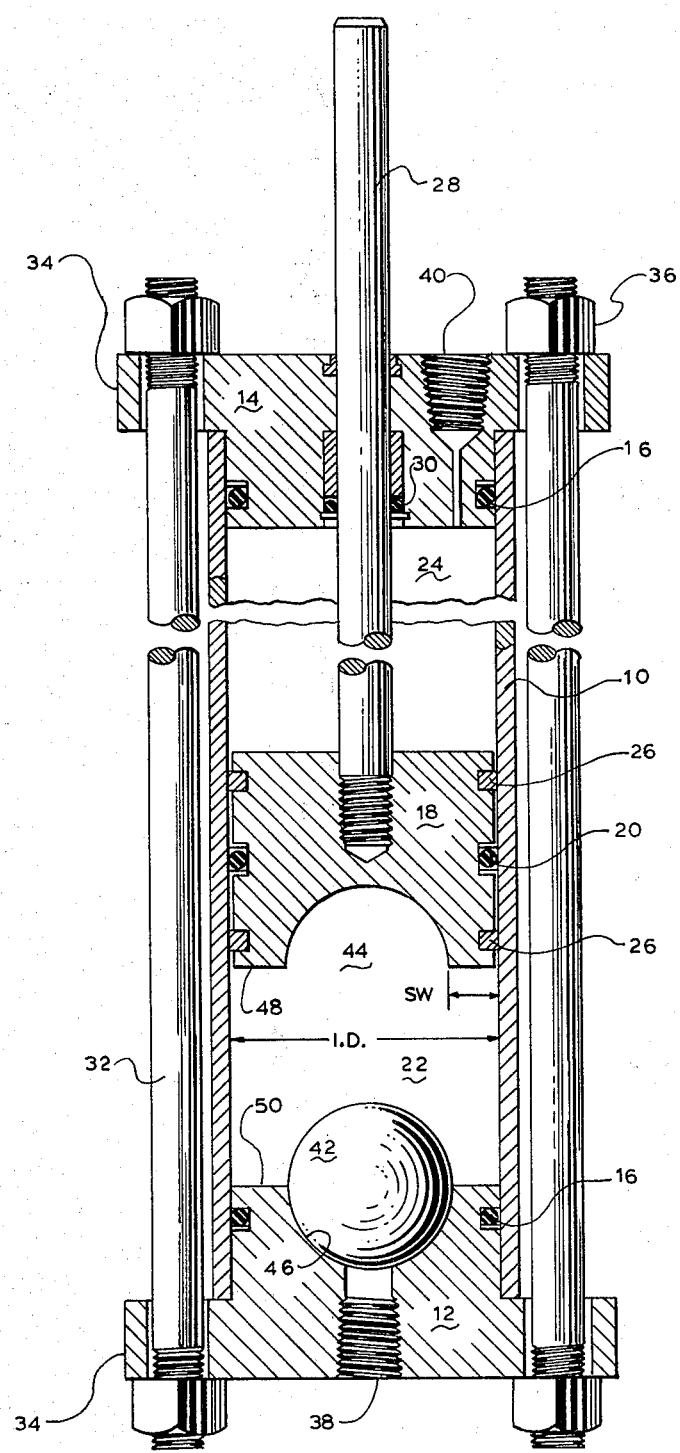

PORTABLE SAMPLE VESSEL

BACKGROUND OF THE INVENTION (1) Field of the Invention

This invention relates to vessels or cells for sampling liquified gasses and more particularly to pre-charged cells for sampling liquified petroleum gasses (LPG).

(2) Description of the Prior Art

As gasses and particularly liquified petroleum gasses, are produced from deep wells and move into pipe lines in the normal course of commerce, it is desired to obtain periodic samples of the gasses for commercial purposes. Equipment for periodically removing samples from a pipe and introducing it in a pre-charged cell are well-known to the industries. For example, see the following U.S. patents.

McKinney et al.—U.S. Pat. No. 2,636,387
Rosenwald—U.S. Pat. No. 3,789,670
Rosenwald—U.S. Pat. No. 3,793,888

As seen by these examples of the prior art, the vessels or cells in which the samples are taken, typically have a cylindrical tube with a sample end and a charge end with a free-floating piston between. The collected liquified gasses will be under considerable pressure. Because the samples are taken over a period of time, there is considerable concern that the different samples of different composition might stratify, so that when a portion of the contents of the cell is removed, a particular stratum would be removed and this would not be a true representation of the total contents of the cell.

Different mixing devices hve been proposed. For example, McKinney et al. discloses a mixing device having a series of dashers connected to a shaft, which extends through a packing gland on one end of a container. (McKinney et al. U.S. Pat. No. 2,636,387; also see Rosenwald U.S. Pat. No. 3,793,888)

Further, it has been suggested that a small ball, similar to a marble placed within an aerosol spray paint can, could be placed within the sample chamber. It is understood that it is desirable that the sample chamber have as small as possible volume when the cell is empty (without a sample). Therefore, when the sample is introduced into the cell, there will be no contamination from residual gasses. Therefore, the ball is fitted into hemispherical recesses formed in the sample end and the piston end. The sample end and piston and have correlative shapes to fit together, so there is a minimum volume when the cell is free of the sample.

SUMMARY OF THE INVENTION (1) New and Different Function

The invention as disclosed herein is an improvement over the prior art, because it is designed so that the cell may have any desired orientation when the piston fits against the sample end.

It will be understood that the purpose of the mixing, is to break up the stratification of the different liquids. All of the liquids are dissolvable, one in the other. However, because the way the liquids are introduced into the sample chamber, it is possible they form strata within the sample chamber. To mix these strata of different liquids, it is only necessary that there be a certain amount of agitation.

This is a different process than the necessity of breaking up sediments, which may form with pigments falling out of suspension in the liquid vehicle of paint. In that situation, it is necessary to have something to dislodge the sediments from a cake-like formation within the chamber. Normally, the aerosol paint cans have a relatively small marble or ball which acts to dislodge the sediments from the bottom or the corners of the paint can.

Since that is not the problem facing the mixing of the LPG sample, it is not necessary to have a small ball.

However, it is necessary that the ball have a specific gravity or density greater than the LPG sample being mixed. This is because the agitation of the sample is by shaking the container, and therefore it is necessary to have the greater density of the ball to cause the movement of the ball within the chamber full of the LPG material.

It will be understood that the sample is drawn from the container in a laboratory. For convenience in operation and the physical limitations of the location, it may be more convenient that the container be placed upon its side. Therefore, it is necessary that as the sample is being drawn from the chamber, the ball not block the movement of the piston toward the sample end of the chamber. This is accomplished by having the ball of larger diameter than one half the chamber. By this construction, the width of the shoulder or ledge around the recess will be less than the radius of the ball. Therefore, as the piston moves toward the sample end, the ball will be forced to roll or move into its seat or recess and will not impede the travel of the piston.

Thus it may be seen that the total function of the combination of elements of this invention far exceeds the sum of the function of the individual components.

(2) Objects of this Invention

An object of this invention is to transport an LPG sample.

Another object of this invention is to mix an LPG sample within the transport vessel.

Further objects are to achieve the above with a device that is sturdy, compact, durable, lightweight, simple, safe, efficient, versatile, ecologically compatible, energy conserving, and reliable, yet inexpensive and easy to manufacture, operate and maintain.

The specific nature of the invention, as well as other objects, uses, and advantages thereof, will clearly appear from the following description and from the accompanying drawing, which is not a scale drawing.

BRIEF DESCRIPTION OF THE DRAWING

The drawing is an axial sectional view of an embodiment of this invention.

DESCRIPTION OF THE PREFERRED EMBODIMENT

Referring to the preferred embodiment, there may be seen a portable sample vessel or container or cell.

Tube 10 is a cylindrical tube of fixed length. One end is closed by sample head or end 12. The other end is closed by charge head or end 14. The sample head 12 and charge head 14 are sealed with head O-ring 16.

Free floating piston 18 is located within the tube 10 between the two heads 12 and 14. Piston O-ring 20 seals the piston 18 to the tube 10 so as to form a gas tight sample chamber 22 between the piston 18 and the sample head 12 and a gas tight charge chamber 24 between the piston 18 and the charge head 14. The piston also has two glide or guide rings 26.

Indicator rod 28 is attached to the piston 18 and extends through charge chamber 24 and charge head 14;

where the indicator rod 28 extends through the charge head 14 it is sealed by rod O-ring 30. In addition, there is present bushing and wiper ring, or excluder around the indicator rod 28.

The heads are held securely in place by the rods 32, which extend through flanges 34 on each of the heads 12 and 14. The heads are secured by nuts 36.

Sample port 38 extends through the sample head 12 and is threaded for standard pipe connections. Charge port 40 extends through the charge head 14 and is also threaded.

Those having ordinary skill in the art will understand that the device as described to this point is basically what is presently available on the market. In use a pre-charge is introduced into the charge chamber 24 through charge port 40. This will be an inert gas, such as nitrogen. The pre-charge will force the piston 18 flush against the sample head 12. Then as the sample is forced into the sample chamber 22, through the sample port 38 it will force the piston 18 upward. The gas in the charge chamber 24 will be further compressed making room for the sample. The distance of the rod 28 from the charge head 14 indicates the volume of sample in the sample chamber 22.

According to this invention, a large mixing ball 42 is placed within the sample chamber 22 at the time of manufacture. Preferably the ball is made of non-metallic material. The specific gravity of the ball must be greater than that of the sample. The mixing ball 42 is a sphere. Piston hemispherical recess 44 is coaxial with the cylindrical tube 10. Also hemicylindrical recess 46 is formed within the sample head 12, coaxial with the tube 10. Therefore ledge or shoulder 48 is formed on the piston 18 around the piston recess 44. Shoulder or ledge 50 is formed upon the sample head 12 around the recess 46. Analysis of the drawing will show that the shoulders 48 and 50 are both radially extending from and symmetrical about the axis of tube 10.

The hemispherical recesses 44 and 46 form a snug fit with the spherical mixing ball 42; there is a minimum volume between the spherical ball 42 and the hemispherical recesses 44 and 46. With the ball 42 within the recesses 44 and 46, the piston forms a minimum volume fit with the sample head 12 when the chamber 22 is empty.

The mixing ball 42 is over one half the inside diameter of the tube 10. Therefore, the diameter of the ball is over twice the width of the shoulders 48 and 50, which are the same width.

Examples of typical dimensions might be that the inside diameter I.D. is 1.75 inches and the diameter of the spherical ball 42 would be 1 inch. I.e. as stated above, the ball diameter of 1 inch is more than ½ the inside diameter (½ of 1.75 inches being 0.875 inches). The hemispherical recesses would also be 1 inch in diameter, or fractionally larger, and therefore the shoulder widths, S.W. would be 0.375 inches, or less. Therefore it may be seen that the diameter of the ball at 1 inch is over twice the shoulder width (twice the shoulder width being no more than 0.75 inches).

Therefore, analysis will show that the stratification of liquids within the sample chamber 22 can be broken up. I.e. the liquid contents of the sample chamber 22 can be mixed by shaking the container causing the movement of the mixing ball 42 to move around within the sample chamber 22. However, also analysis will show that as the piston 18 moves toward the sample head 12, the mixing ball 42 cannot block the movement of the piston.

I.e. if the ball were laying against the tube 10, then the movement of the piston would move upon a sloping part of the ball forcing the ball into the hemispherical recesses 44 and 46 as the piston 18 continued to move toward the sample head 12. Obviously, the edges between the recess 44 and shoulder 48 or the edge between the recess 46 and the shoulder 50 could be beveled. However, it is desirable to keep this beveling at a minimum so as not to increase the volume of the chamber 22 when the piston makes a limit move toward the sample head 12. If the effective shoulder width S.W. appears to be too large, the better practice to reduce the shoulder width would be to use a larger mixing ball 42 rather than by forming bevels.

The embodiment shown and described above is only exemplary. I do not claim to have invented all the parts, elements or steps described. Various modifications can be made in the construction, material, arrangement, and operation, and still be within the scope of my invention.

The limits of the invention and the bounds of the patent protection are measured by and defined in the following claims. The restrictive description and drawing of the specific example above do not point out what an infringement of this patent would be, but are to enable the reader to make and use the invention.

As an aid to correlating the terms of the claims to the exemplary drawing, the following catalog of elements is provided:

10 tube
12 sample head
14 charge head
16 head O-ring
18 piston
20 piston O-ring
22 sample chamber
24 charge chamber
26 guide ring
28 indicator rod
30 rod O-ring
32 tie rods
34 flanges
36 nuts
38 sample port
40 charge port
42 mixing ball
44 piston recess
46 head recess
48 shoulder
50 shoulder
I.D. inside diameter
S.W. shoulder width

I claim as my invention:

1. A cell for collecting samples of liquified gasses having
   a. a cylindrical container with an inside diameter having
      (i) a sample end, and
      (ii) a charge end,
      (iii) each of which is closed,
   b. a piston in the container,
   c. a sample port at the sample end for introducing samples into the container between the sample end and the piston,
   d. a charge port in the charge end for introducing an inert gas charge into the container between the charge end and the piston, and
   e. a ball in the container between the sample end and the piston;

wherein the improvement comprises:
- f. the ball having a diameter over half the inside diameter of the cylinder,
- g. the piston and sample end having hemispherical recesses into which the ball snugly fits, said hemispherical recesses coaxial with the cylinder, and
- h. shoulders around the recesses both radially extending from and symmetrical about the axis of the cylinder, each shoulder having a width of less than one half the diameter of the ball so that the ball cannot rest on the shoulder but enters the recesses upon discharge of sample from the container.

* * * * *